(12) United States Patent
Diehl

(10) Patent No.: US 6,770,180 B1
(45) Date of Patent: Aug. 3, 2004

(54) ELECTROCHEMICAL MEASURING SENSOR

(75) Inventor: Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 110 days.

(21) Appl. No.: 09/913,482

(22) PCT Filed: Nov. 23, 2000

(86) PCT No.: PCT/DE00/04149

§ 371 (c)(1),
(2), (4) Date: Nov. 26, 2001

(87) PCT Pub. No.: WO01/44797

PCT Pub. Date: Jun. 21, 2001

(30) Foreign Application Priority Data

Dec. 15, 1999 (DE) ......................................... 199 60 329

(51) Int. Cl.[7] ............................................... G01N 27/41
(52) U.S. Cl. ........................ 204/424; 204/426; 204/425
(58) Field of Search ................................. 204/421–429

(56) References Cited

U.S. PATENT DOCUMENTS

| 3,843,400 | A | * | 10/1974 | Radford et al. |
|---|---|---|---|---|
| 4,283,441 | A | | 8/1981 | Haecker et al. |
| 4,379,741 | A | * | 4/1983 | Sano et al. |
| 4,588,494 | A | * | 5/1986 | Kato et al. |
| 4,668,375 | A | * | 5/1987 | Kato et al. |
| 4,943,330 | A | * | 7/1990 | Iino et al. |
| 5,314,604 | A | * | 5/1994 | Friese et al. |
| 5,435,901 | A | * | 7/1995 | Friese et al. |
| 5,662,786 | A | * | 9/1997 | Friese et al. |
| 5,895,591 | A | * | 4/1999 | Kojima et al. |
| 6,436,277 | B2 | * | 8/2002 | Schnaibel et al. |

FOREIGN PATENT DOCUMENTS

| DE | 198 37 607 | 7/1999 |
|---|---|---|
| EP | 0 880 026 | 11/1998 |

\* cited by examiner

Primary Examiner—Kaj K. Olsen
(74) Attorney, Agent, or Firm—Kenyon & Kenyon

(57) ABSTRACT

An electrochemical sensor for determining a gas concentration of a measuring gas using a sensor element that has at least one electrode situated on an ion-conducting solid electrolyte body, an electrode lead leading to the electrode. The electrode lead is made of a material possessing no ionic conductivity or an ionic conductivity that is significantly less in comparison with the material of the electrode, and/or having a low resistance.

28 Claims, 3 Drawing Sheets

ELECTROCHEMICAL MEASURING SENSOR

FIELD OF THE INVENTION

The present invention is based on an electrochemical sensor.

BACKGROUND INFORMATION

The sensors of this species must be heated in the active range to temperatures of more than ca. 350° C. to achieve the necessary ionic conductivity of the solid electrolyte body. To increase the measuring accuracy of the sensor, it is known to control and, if necessary, to adjust the operating temperature of the measuring cell, i.e., of the solid electrolyte body in the measuring region. To this end, it is known to assign a heating device to the sensor, the heating device being capable of being switched on and off as a function of an operating temperature measured at the measuring cell.

To determine the operating temperature of the measuring cell, it is known to apply an a.c. voltage to the sensor and to use a measuring device to determine a total alternating-current resistance made up of the conjugate impedances of the solid electrolyte body and of the corresponding electrodes and electrode leads. The temperature-dependent internal resistance of the solid electrolyte body in the measuring region and, as such, its temperature in the measuring region can be deduced from the total resistance.

In the known method, it is disadvantageous that the measuring device, which determines the temperature-dependent resistance of the solid electrolyte body, uses a constant resistance of the electrodes and the electrode leads as a baseline. However, the resistance of the electrode leads and the electrodes is subject to a relatively high degree of scatter due to manufacture.

The measuring device adds this not insignificant scatter error to a temperature-dependent change in the resistance of the solid electrolyte body in the measuring region and provides a corresponding faulty control signal for the heating device of the sensor. As a result, the sensor is adjusted to an incorrect operating temperature.

It is further disadvantageous that, in the lead region, the solid electrolyte body forms an additional internal resistance that is connected in parallel to the internal resistance of the solid electrolyte body in the region of the electrodes (measuring region) and also makes a not insignificant contribution to the total resistance. If, in addition, the temperature in the lead region is higher than in the measuring region, the internal resistance of the solid electrolyte body in the lead region is reduced, and it makes a contribution to the total resistance that is dependent on the temperature of the solid electrolyte body in the lead region. As a result, the sensor is likewise adjusted to an incorrect operating temperature.

To avoid the effect of the internal resistance in the lead region, it is known from German Published Patent Application No. 198 37 607 to provide the lead of an electrode opposite the lead region of the solid electrolyte body with an electrically insulating layer. This design has the disadvantage that the use of at least one insulating layer additionally requires at least one printing step and is, therefore, expensive from a standpoint of production engineering.

SUMMARY OF THE INVENTION

In comparison with the related art, the electrochemical sensor according to the present invention has the advantage of an improved regulation of the operating temperature, thereby enabling the sensor to function more precisely and more uniformly.

An exemplary embodiment and/or exemplary method of the present invention provides that the internal resistance of a solid electrolyte body in a lead region between the electrode leads situated on the solid electrolyte body is significantly higher than the internal resistance of the solid electrolyte body in a measuring region between the corresponding electrodes. Thus, the contribution to the total resistance made by the internal resistance in the lead region of the solid electrolyte body, which is connected in parallel to the internal resistance in the measuring region of the solid electrolyte body, is significantly reduced. Thus, the influence of the internal resistance in the lead region on the temperature regulation may be negligible. Additionally, from a standpoint of production engineering, an electrically insulating layer may be dispensed with so that a printing step may no longer be required.

According to the present invention, the resistance of at least one electrode lead makes a small contribution to the total resistance. Furthermore, the electrode lead is made of a material having a smaller degree of processing scatter with respect to its resistance. Thus, the effect of the resistance of the electrode lead on the total resistance is smaller. The present invention additionally improves the regulation of the operating temperature of the sensor.

Designing the internal pump electrode lead and/or the reference electrode lead using a material having a lesser ionic conductivity or no ionic conductivity in comparison with the electrode in question has the additional advantage that the resistive coupling of the particular electrode leads that can lead to a loading effect of the pump voltage on the measuring voltage of the sensor cell is prevented. As a result, the lambda=1-ripple is decreased or even prevented, thereby further improving the control dynamic response of the sensor.

An additional advantage results from designing the external pump electrode lead and/or the internal pump electrode lead using a material having a low resistance in comparison with the material of the electrode in question. As a result, the drop in the pump voltage in the external pump electrode lead and/or internal pump electrode is reduced, thereby improving pump function.

A particular embodiment of the present invention provides that the reference electrode lead is situated in the layer plane of the heater, thereby eliminating at least one printing step. In a further embodiment of the present invention, the heater and reference electrode lead are produced from the same material, thereby resulting in an additional advantage from a standpoint of production engineering.

DETAILED DESCRIPTION

Figure 1:
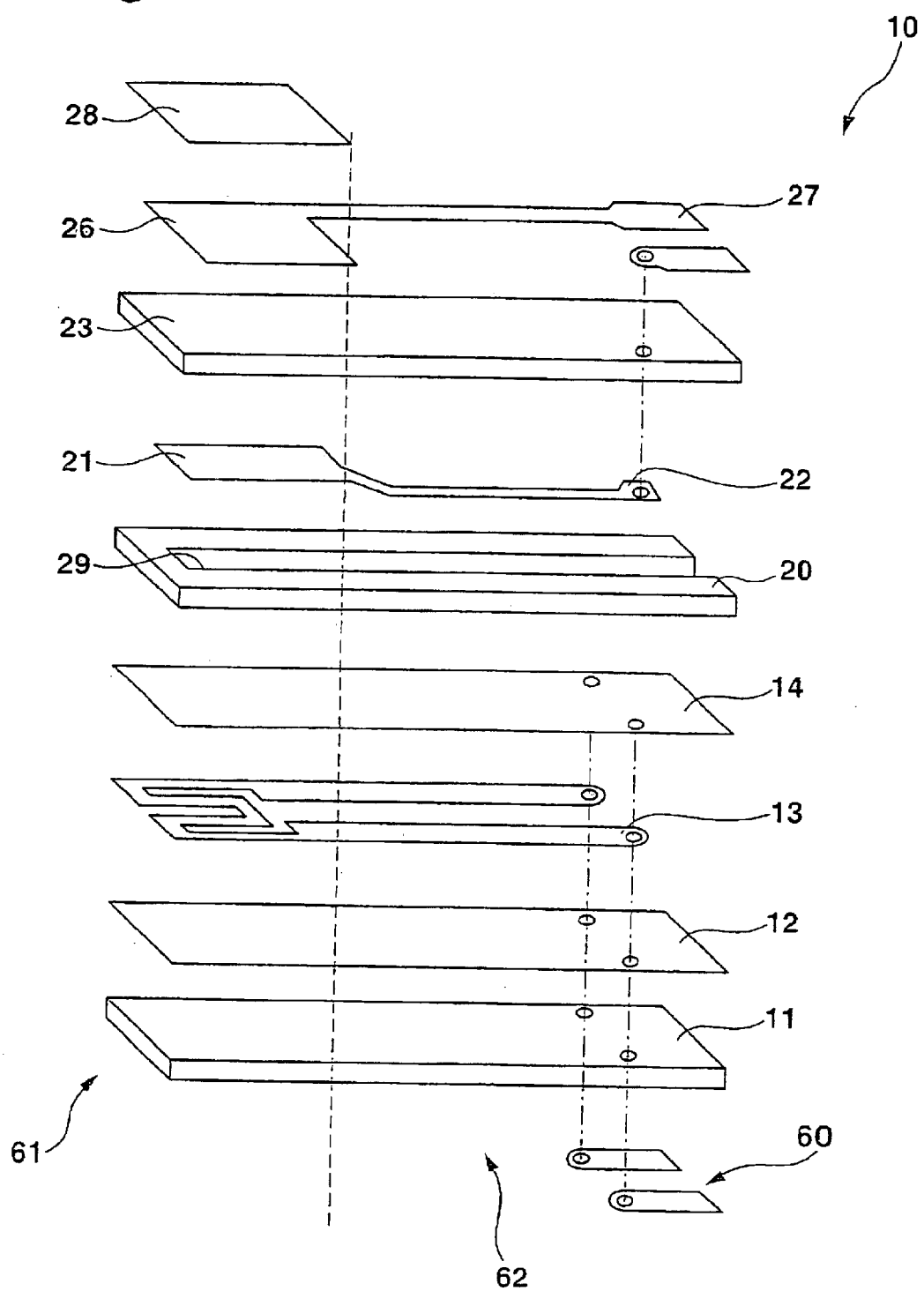
FIG. 1 shows an exploded view of a first exemplary embodiment of a sensor.

FIG. 1 shows an electrochemical sensor for analyzing gases, in the form of a planar sensor element 10. Sensor element 10 including a measuring region 61 and a lead region 62 has electrical connection contacts 60, a first solid electrolyte foil 11 designated as a heating foil, an insulating layer 12, a heater 13, an additional insulating layer 14, a second solid electrolyte foil 20 designated as a reference gas duct foil, as well as a reference electrode 21 having a reference electrode lead 22. Formed in reference gas duct foil 20 is a reference gas duct 29, which is connected via an opening in the lead region to air as a reference gaseous atmosphere. Above reference electrode 21 and reference electrode lead 22, the sensor element further has a third solid electrolyte foil 23 designated as a measuring foil, a measuring electrode 26 including measuring electrode lead 27, as well as a porous protective layer 28.

Figure 2:
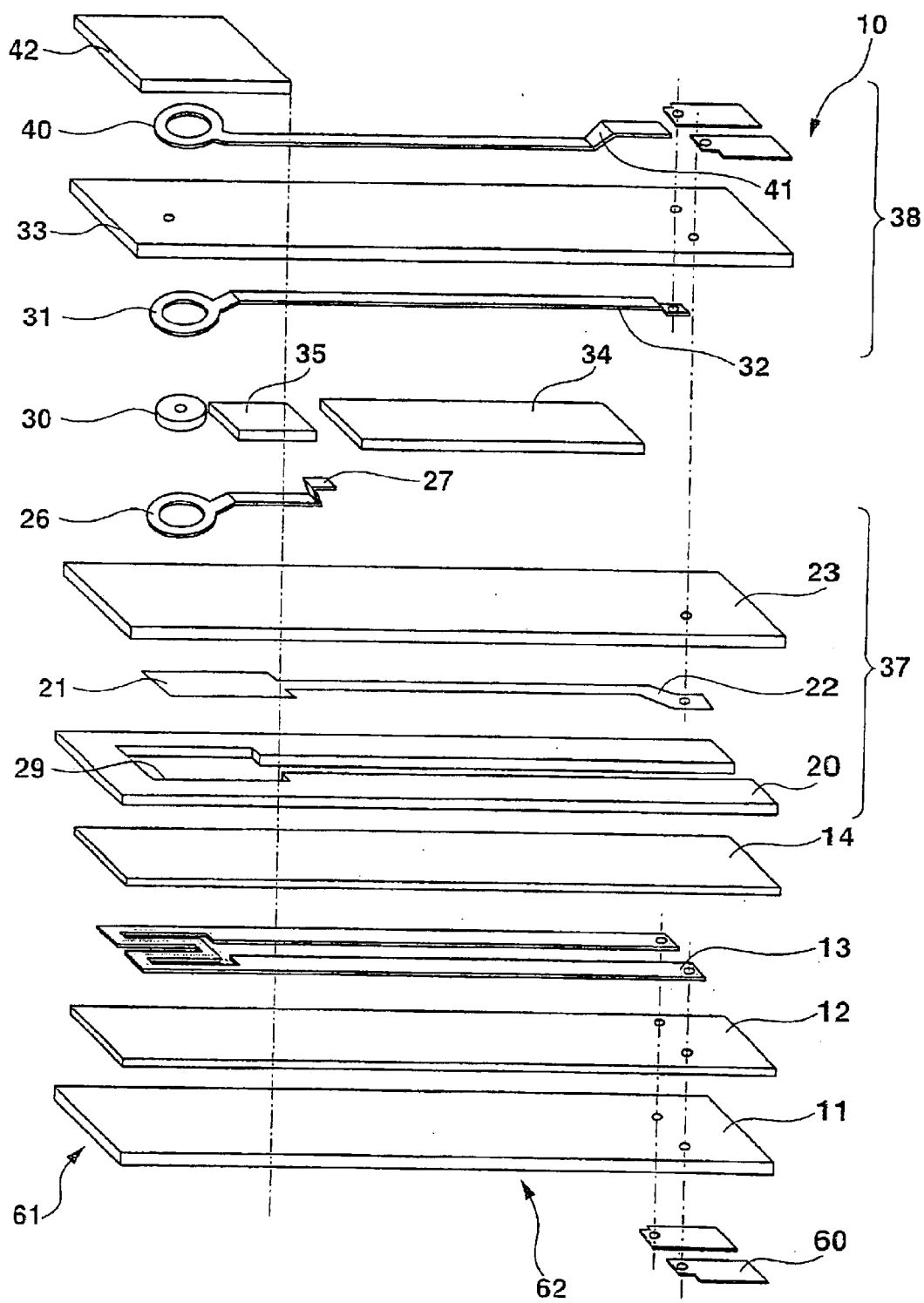
FIG. 2 shows an exploded view of an additional exemplary embodiment of a sensor.

FIG. 2 shows an additional exemplary embodiment of an electrochemical sensor for analyzing gases. This sensor is a so-called broadband probe having two cells 37, 38. First cell 37 is a concentration cell that functions according to the Nernst principle. The operating mode of first cell 37 corresponds with the sensor described in FIG. 1. Therefore, the same reference numerals are used for the same elements in FIG. 2. Second cell 38 is an electrochemical pump cell that is laminated together with first cell 37 and that cooperates with the concentration cell in a method known per se, according to the functional principle of the broadband probe. Situated in the junction region between first cell 37 and second cell 38 is an intermediate layer 35 and a filler layer 34 for forming a space (not further represented) for accommodating diffusion barrier 30. Second cell 38 has an internal pump electrode 31, including an internal pump electrode lead 32, a fourth solid electrolyte foil 33 designated as a pump foil, an external pump electrode 40, including an external pump electrode lead 41, and a porous protective layer 42. Measuring electrode lead 27 and internal pump electrode lead 32 run together in lead region 62 of sensor element 10.

Figure 3:
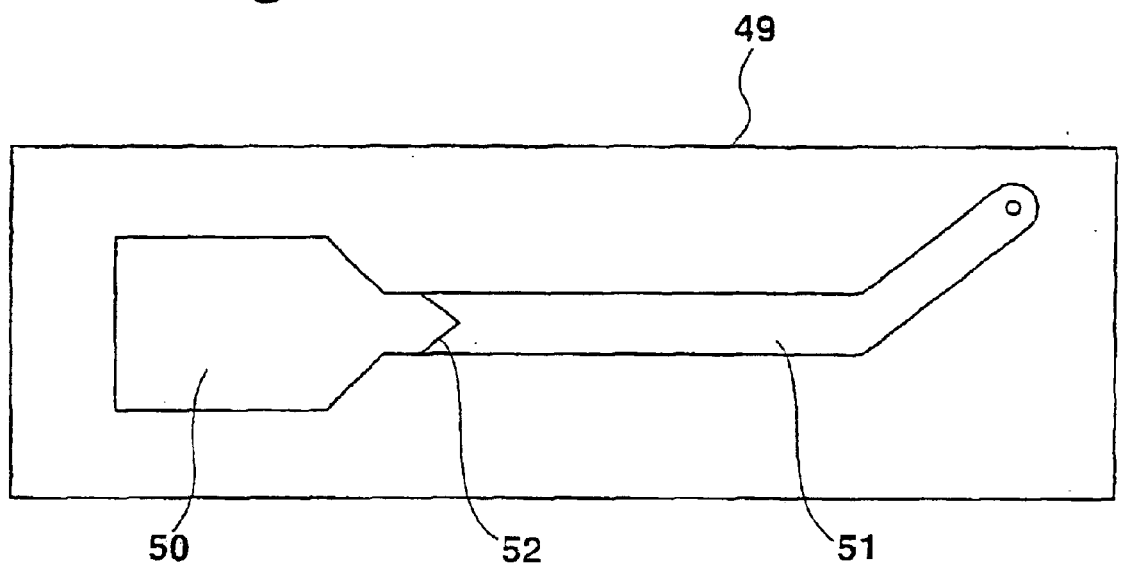
FIG. 3 shows a top view of an electrode including an electrode lead of a sensor.

FIG. 3 shows a large surface of a solid electrolyte foil 49 having an electrode 50 and an electrode lead 51, which can, for example, form measuring electrode 26, including measuring electrode lead 27, or reference electrode 21, including reference electrode lead 22, of the sensor shown in FIG. 1. The electrode 50 shown in FIG. 3, including electrode lead 51, can, for example, also represent external pump electrode 40, including external pump electrode lead 41, internal pump electrode 31, including internal pump electrode lead 32, measuring electrode 26, including measuring electrode lead 27, or reference electrode 21, including reference electrode lead 22, of the sensor shown in FIG. 2.

Electrode lead 51 is made of an electrically conductive material, preferably platinum, and has a ceramic component for mechanical stabilization of 7% by volume $Al_2O_3$, for example. Electrode 50 is made of a catalytic material, preferably platinum, and a ceramic material, preferably 20% by volume $ZrO_2$ stabilized with $Y_2O_3$. In an additional embodiment, electrode 50 further has a porosity produced by a pore-forming material. The junction between electrode 50 and electrode lead 51 is produced by a wedge-shaped junction region 52 having an overlap zone. Electrode 50 and electrode lead 51 are produced according to a method known per se, e.g. by screen printing.

The described design can be used in any combination for every electrode shown in FIGS. 1 and 2 and for the respective electrode leads. It is conceivable to also use the described design of electrode 50 including electrode lead 51 for other electrochemical sensors of this type.

In the exemplary embodiment for the broadband probe (FIG. 2), internal pump electrode lead 32 and/or reference electrode lead 22 are produced using $Al_2O_3$ as the ceramic component to reduce the lambda=1–ripple. In comparison with the $ZrO_2$ stabilized with $Y_2O_3$, which is suitable as the ceramic material for electrode 21, 31, the $Al_2O_3$ possesses no ionic conductivity. As a result, there is no ionic conduction between electrode leads 22, 32, thereby increasing the internal resistance in this region.

A further exemplary embodiment of a broadband probe (FIG. 2) is that to reduce the drop in pump voltage in the lead region, external pump electrode lead 41 features a material having a low resistance in comparison with the material of external pump electrode 40. This is achieved in that the proportion of electrically conductive material, e.g. platinum, is higher in the cermet material of external pump electrode lead 41 than in external pump electrode 40.

Figure 4:
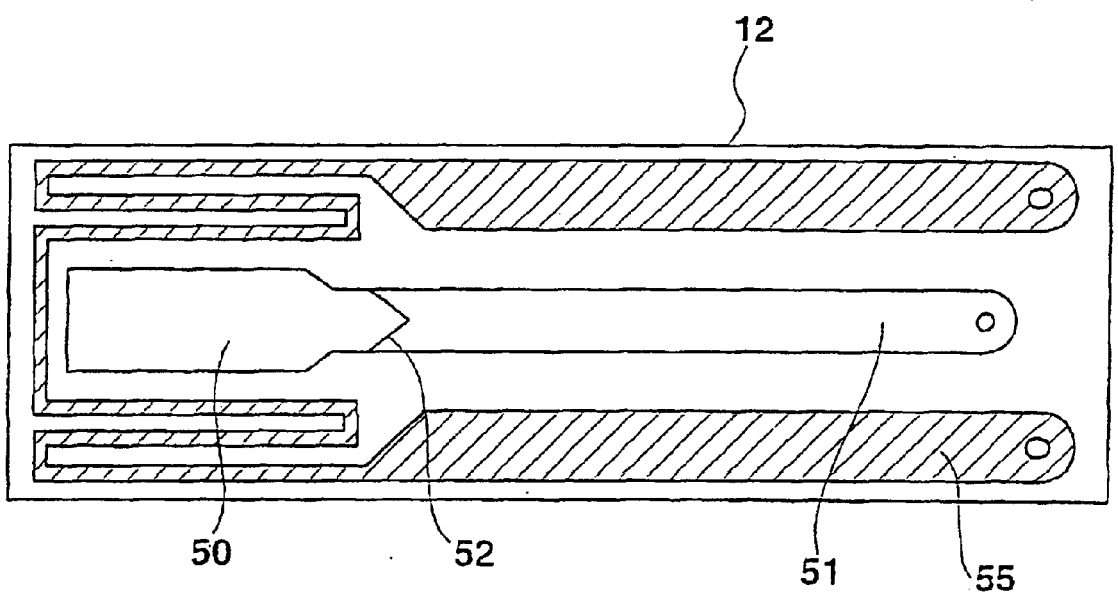
FIG. 4 shows a top view of an electrode including an electrode lead as well as a heater.

FIG. 4 represents an additional specific embodiment in which electrode 50 and electrode lead 51, including a junction region 52, are situated in a layer plane in which a heater 55 embedded in the solid electrolyte body is located. For this purpose, heater 55, electrode 50, and electrode lead 55 are pressed onto first insulation layer 12, for example. In a preferred embodiment, heater 55 is produced from the same material as electrode lead 51.

What is claimed is:

1. An electrochemical sensor for determining at least one of a gas component and a gas concentration in a gas mixture, comprising:
   an ion-conducting solid electrolyte body;
   at least one electrode situated on the ion-conducting solid electrolyte body; and
   an electrode lead leading to the at least one electrode, wherein the electrode lead includes a material that possesses one of no ionic conductivity and an ionic conductivity that is significantly less than that of a material of the at least one electrode so that an internal resistance of the ion-conducting solid electrolyte body in a lead region of the sensor is significantly greater than an internal resistance of the solid electrolyte body in a measuring region of the sensor.

2. The electrochemical sensor according to claim 1, wherein:
   the at least one electrode and the electrode lead are each formed from a cermet material, and
   a ceramic component of the at least one electrode is different than a ceramic component of the electrode lead.

3. The electrochemical sensor according to claim 2, wherein:
   the ceramic component of the electrode lead contains 5–10% by volume $Al_2O_3$.

4. The electrochemical sensor according to claim 2, wherein:
   the ceramic component of the electrode contains 10–60% by volume $ZrO_2$ stabilized with $Y_2O_3$.

5. The electrochemical sensor according to claim 4, wherein:
   the ceramic component of the electrode contains 20% by volume $ZrO_2$ stabilized with $Y_2O_3$.

6. The electrochemical sensor according to claim 4, wherein the at least one electrode includes a pore-forming material to increase a porosity of the at least one electrode.

7. The electrochemical sensor according to claim 2, wherein:
   at least one of a metallic component of the at least one electrode and a metallic component of the electrode lead includes Pt.

8. The electrochemical sensor according to claim 1, further comprising:
a wedge-shaped junction region including an overlap zone and being formed between the electrode lead and the at least one electrode.

9. The electrochemical sensor according to claim 1, further comprising:
a heater; and
a layer plane in which the heater embedded in the ion-conducting solid electrolyte body is located, wherein:
at least one of the electrode lead and the at least one electrode is situated in the layer plane.

10. The electrochemical sensor according to claim 9, wherein:
the heater is made of a material that is the same as the material of the electrode lead.

11. The electrochemical sensor according to claim 1, wherein the at least one electrode includes at least one of an internal pump electrode and a reference electrode, the internal pump electrode and the reference electrode being configured with corresponding electrode leads of a measuring cell.

12. The electrochemical sensor according to claim 1, wherein a "lambda=1—ripple" is at least decreased.

13. The electrochemical sensor according to claim 1, wherein the internal resistance of the ion-conducting solid electrolyte body does not impact a temperature regulation of the electrochemical sensor.

14. The electrochemical sensor according to claim 1, wherein the at least one electrode and electrode lead are formed by screen printing.

15. An electrochemical sensor for determining at least one of a gas component and a gas concentration in a gas mixture, comprising:
an ion-conducting solid electrolyte body;
at least one electrode situated on the ion-conducting solid electrolyte body; and
an electrode lead leading to the at least one electrode, wherein the electrode lead includes a material having a low resistance in comparison with a material of the at least one electrode so that a resistance of the electrode lead is less than a resistance of the electrode;
wherein:
the at least one electrode and the electrode lead are each formed from a cermet material, and
a ceramic component of the at least one electrode is different than a ceramic component of the electrode lead.

16. The electrochemical sensor according to claim 15, wherein:
the ceramic component of the electrode lead contains 5–10% by volume $Al_2O_3$.

17. The electrochemical sensor according to claim 15, wherein:
the ceramic component of the electrode contains 10–60% by volume $ZrO_2$ stabilized with $Y_2O_3$.

18. The electrochemical sensor according to claim 17, wherein:
the ceramic component of the electrode contains 20% by volume $ZrO_2$ stabilized with $Y_2O_3$.

19. The electrochemical sensor according to claim 17, wherein the at least one electrode includes a pore-forming material to increase a porosity of the at least one electrode.

20. The electrochemical sensor according to claim 15, wherein:
at least one of a metallic component of the at least one electrode and a metallic component of the electrode lead includes Pt.

21. The electrochemical sensor according to claim 15, further comprising:
wherein the at least one electrode includes at least one of an internal pump electrode and a reference electrode, the internal pump electrode and reference electrode being configured with corresponding electrode leads of a measuring cell.

22. An electrochemical sensor for determining at least one of a gas component and a gas concentration in a gas mixture, comprising:
an ion-conducting solid electrolyte body;
at least one electrode situated on the ion-conducting solid electrolyte body;
an electrode lead leading to the at least one electrode, wherein the electrode lead includes a material having a low resistance in comparison with a material of the at least one electrode so that a resistance of the electrode lead is less than a resistance of the electrode; and
a wedge-shaped junction region including an overlap zone and being formed between the electrode lead and the at least one electrode.

23. An electrochemical sensor for determining at least one of a gas component and a gas concentration in a gas mixture, comprising:
an ion-conducting solid electrolyte body;
at least one electrode situated on the ion-conducting solid electrolyte body;
an electrode lead leading to the at least one electrode, wherein the electrode lead includes a material having a low resistance in comparison with a material of the at least one electrode so that a resistance of the electrode lead is less than a resistance of the electrode;
a heater; and
a layer plane in which the heater embedded in the ion-conducting solid electrolyte body is located;
wherein at least one of the electrode lead and the at least one electrode is situated in the layer plane.

24. The electrochemical sensor according to claim 23, wherein:
the heater is made of a material that is the same as the material of the electrode lead.

25. An electrochemical sensor for determining at least one of a gas component and a gas concentration in a gas mixture, comprising:
an ion-conducting solid electrolyte body;
at least one electrode situated on the ion-conducting solid electrolyte body; and
an electrode lead leading to the at least one electrode, wherein:
the electrode lead includes a material having a low resistance in comparison with a material of the at least one electrode so that a resistance of the electrode lead is less than a resistance of the electrode, and
the material possesses one of no ionic conductivity and an ionic conductivity that is significantly less in comparison with the material of the at least one electrode so that an internal resistance of the ion-conducting solid electrolyte body in a lead region of the sensor is significantly greater than an internal resistance of the solid electrolyte body in a measuring region of the sensor.

26. The electrochemical sensor according to claim 25, further comprising:

a wedged-shaped junction region including an overlap zone and being formed between the electrode lead and the at least one electrode.

27. The electrochemical sensor according to claim 26, further comprising:

a heater; and a layer plane in which the heater embedded in the ion-conducting solid electrolyte body is located, wherein at least one of the electrode lead and the at least one electrode is arranged in the same layer plane.

28. The electrochemical sensor according to claim 27, wherein the at least one electrode includes at least one of an internal pump electrode and a reference electrode, the internal pump electrode and reference electrode being configured with corresponding electrode leads of a measuring cell.

* * * * *